US00PP15326P2

(12) United States Plant Patent
Gitzels

(10) Patent No.: US PP15,326 P2
(45) Date of Patent: Nov. 16, 2004

(54) ***DAHLIA* PLANT NAMED 'BALNOVBURS'**

(50) Latin Name: *Dahlia variabilis*
Varietal Denomination: Balnovburs

(75) Inventor: Jeroen Gitzels, Rijsenhout (NL)

(73) Assignee: Ball Horticulture Co., West Chicago, IL (US)

( * ) Notice: Subject to any disclaimer, the term of this patent is extended or adjusted under 35 U.S.C. 154(b) by 0 days.

(21) Appl. No.: 10/753,811

(22) Filed: Jan. 8, 2004

(51) Int. Cl.[7] ..... A01H 5/00
(52) U.S. Cl. ..... Plt./321
(58) Field of Search ..... Plt./321

*Primary Examiner*—Anne Marie Grunberg
*Assistant Examiner*—June Hwu
(74) *Attorney, Agent, or Firm*—C. A. Whealy

(57) ABSTRACT

A new and distinct cultivar of *Dahlia* plant named 'Balnovburs', characterized by its upright plant habit; freely branching habit; semi-double type inflorescences; and yellow and red-colored ray florets.

1 Drawing Sheet

Botanical classification/cultivar designation: *Dahlia variabilis* cultivar Balnovburs.

BACKGROUND OF THE INVENTION

The present Invention relates to a new and distinct cultivar of *Dahlia* plant, botanically known as *Dahlia variabilis*, commercially referred to as a pot-type *Dahlia*, and hereinafter referred to by the cultivar name 'Balnovburs'.

The new *Dahlia* is a product of a planned breeding program conducted by the Inventor in Enkhuizen, The Netherlands. The new *Dahlia* originated from a cross-pollination made by the Inventor in 1997 of two unidentified proprietary selections of *Dahlia variabilis*, not patented. The cultivar Balnovburs was discovered and selected by the Inventor as a flowering plant within the progeny of the stated cross-pollination in a controlled environment in Enkhuizen, The Netherlands in October, 1997.

Asexual reproduction of the new *Dahlia* by stem cuttings was first conducted in Enkhuizen, The Netherlands in 1999. Asexual reproduction by cuttings has shown that the unique features of this new *Dahlia* are stable and reproduced true to type in successive generations.

SUMMARY OF THE INVENTION

The cultivar Balnovburs has not been observed under all possible environmental conditions. The phenotype may vary somewhat with variations in environment such as temperature and daylength, without, however, any variance in genotype.

The following traits have been repeatedly observed and are determined to be the unique characteristics of 'Balnovburs'. These characteristics in combination distinguish 'Balnovburs' as a new and distinct pot-type *Dahlia:*

1. Upright plant habit.
2. Freely branching habit.
3. Semi-double type inflorescences.
4. Yellow and red-colored ray florets.

Plants of the new *Dahlia* differ from plants of the parent selections primarily in ray floret coloration as plants of the parent selections do not have yellow and red-colored ray florets.

Plants of the new *Dahlia* can be compared to plants of the *Dahlia* cultivar Balnovches, disclosed in U.S. Plant Pat. No. 14,254. In side-by-side comparisons conducted in West Chicago, Ill., plants of the new *Dahlia* were larger, more vigorous and had fewer ray florets per inflorescence than plants of the cultivar Balnovches. In addition, plants of the new *Dahlia* and the cultivar Balnovches differed in ray floret coloration.

BRIEF DESCRIPTION OF THE PHOTOGRAPHS

The accompanying colored photographs illustrate the overall appearance of the new *Dahlia* showing the colors as true as it is reasonably possible to obtain in colored reproductions of this type. Colors in the photographs may differ from the color values cited in the detailed botanical description which accurately describe the colors of the new *Dahlia.*

The photograph at the top of the sheet comprises a side perspective view of a typical flowering plant of 'Balnovburs'.

The photograph at the bottom of the sheet is a close-up view of a typical inflorescence of 'Balnovburs'.

DETAILED BOTANICAL DESCRIPTION

In the following description, color references are made to The Royal Horticultural Society Colour Chart, 2001 Edition, except where general terms of ordinary dictionary significance are used. The following observations and measurements describe plants grown and flowered during the spring in West Chicago, Ill., under commercial practice in a polycarbonate-covered greenhouse. During the production the plants, day temperatures ranged from 18 to 24° C., night temperatures ranged from 16 to 18° C., and light levels ranged from 4,000 to 6,000 footcandles. One cutting was planted per 10-cm container and plants were grown for about 12 weeks.

Botanical classification: *Dahlia variabilis* cultivar Balnovburs.

Parentage:

*Female, or seed, parent.*—Unidentified selection of *Dahlia variabilis,* not patented.

*Male, or pollen, parent.*—Unidentified selection of *Dahlia variabilis,* not patented.

Propagation:

*Type.*—By stem cuttings.

*Time to rooting.*—About 7 days at 18° C.

*Time to develop a rooted cutting.*—About 21 days at 18° C.

*Root description.*—Fibrous; development of tubers has not been observed.

Plant description:

*Appearance.*—Herbaceous pot-type *Dahlia*. Inverted triangle; upright plant habit. Freely branching, about four to five lateral branches per plant; pinching will enhance branching. Moderately vigorous.

*Plant height* (*soil level to top of foliage*).—About 20.3 cm.

*Plant height* (*soil level to top of inflorescences*).—About 28 cm.

*Plant width or area of spread.*—About 20.8 cm.

*Lateral branches.*—Length: About 10 cm. Diameter: About 5 mm. Internode length: About 4 cm. Strength: Strong. Texture: Smooth, glabrous. Color: 144A.

*Foliage description.*—Arrangement: Opposite; simple. Length: About 7.2 cm. Width: About 4 cm. Shape: Ovate. Apex: Acute. Base: Attenuate. Margin: Serrate. Texture, upper surface: Leathery; rugose; sparsely pubescent along midvein. Texture, lower surface: Leathery; rugose; smooth, glabrous. Venation pattern: Pinnate. Petiole length: About 3 cm. Petiole diameter: About 4 mm. Petiole texture, upper and lower surfaces: Smooth, glabrous. Color: Developing foliage, upper surface: N134A. Developing foliage, lower surface: 138A. Fully expanded foliage, upper surface: 138A. Fully expanded foliage, lower surface: 138B. Venation, upper and lower surfaces: 144B. Petiole, upper and lower surfaces: 144B.

Inflorescence description:

*Appearance.*—Terminal semi-double type inflorescences held above and beyond the foliage on strong flexible peduncles; inflorescences face mostly upright to slightly outwardly. Composite inflorescence form with ovate-shaped ray florets and disc florets massed at the center; ray and disc florets develop acropetally on a capitulum. Inflorescences not fragrant. Inflorescences persistent.

*Flowering response.*—Plants flower continuous and freely from spring through fall.

*Postproduction longevity.*—Inflorescences maintain good color and substance for about seven to ten days on the plant.

*Quantity of inflorescences.*—One fully opened inflorescence per peduncle at a time.

*Inflorescence bud* (*stage of showing color*).—Shape: Oblate. Length: About 1.9 cm. Diameter: About 1.6 cm. Color: 151D.

*Inflorescence size.*—Diameter: About 7.3 cm. Depth (height): About 2.5 cm. Disc diameter: About 2 cm.

*Ray florets.*—Shape: Ovate. Aspect: Straight, concave. Length: About 3.8 cm. Width: About 1 cm. Apex: Emarginate to acute. Base: Fused into a short corolla tube. Margin: Entire. Texture, upper and lower surfaces: Smooth, glabrous. Quantity per inflorescence: About eight true ray florets in a single whorl. Each ray floret has three to four petal-like structures that originate from the corolla tube opening. These structures are about 2.8 cm in length and about 2 to 3 mm in width. Color: When opening and fully opened, upper surface: 34A; towards the apex, close to 2B; color becoming closer to 179B with development. When opening and fully opened, lower surface: 2B. Petal-like structures, upper and lower surfaces: 1A to 1B with sectors of 34A.

*Disc florets.*—Shape: Tubular, elongated. Apex: Five-pointed. Length: About 1 cm. Width: About 2 mm. Quantity per inflorescence: About 52. Color: 12A.

*Involucral bracts.*—Quantity per inflorescence: About seven. Length: About 2 cm. Width: About 5 mm. Shape: Lanceolate. Apex: Acute. Base: Truncate. Margin: Entire. Texture, upper and lower surfaces: Smooth, glabrous. Color, upper and lower surfaces: Towards the base, 143A; gradually fading closer to 145B towards the apex.

*Peduncles.*—Length: About 10.4 cm. Diameter: About 2 mm. Strength: Strong, flexible. Aspect: Erect. Texture: Smooth, glabrous. Color: 144A.

*Reproductive organs.*—Androecium: Present on disc florets only. Quantity per floret: One. Anther length: About 2.6 mm. Anther color: 162A. Pollen amount: Moderate. Pollen color: 17A. Gynoecium: Present on both ray and disc florets. Quantity per floret: One. Pistil length: About 8 mm. Stigma color: 16A. Style length: About 2.5 mm. Style color: 145D. Ovary color: 145B.

*Seed/fruit.*—Seed and fruit production has not been observed.

Disease/pest tolerance: Plants of the new *Dahlia* have not been observed to be tolerant to pathogens and pests common to *Dahlias.*

It is claimed:

1. A new and distinct cultivar of *Dahlia* plant named 'Balnovburs', as illustrated and described.

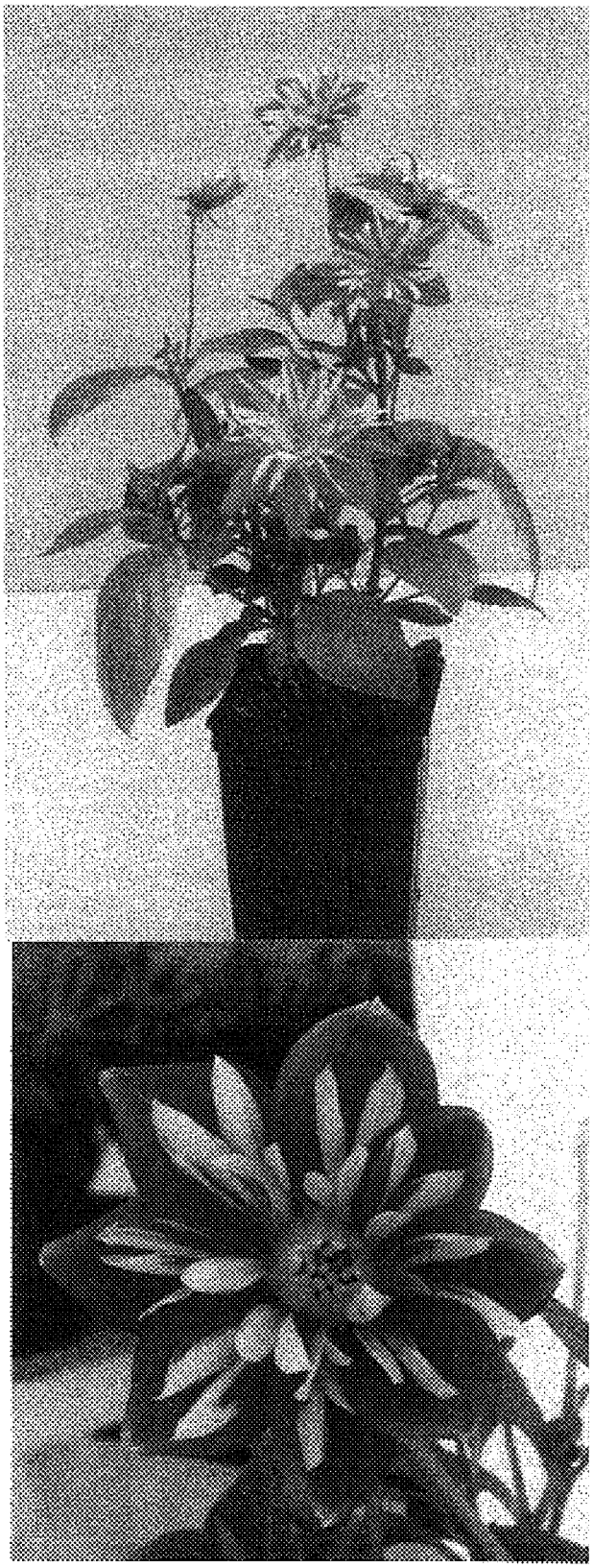

* * * * *